US011455741B2

(12) United States Patent
Yang et al.

(10) Patent No.: US 11,455,741 B2
(45) Date of Patent: Sep. 27, 2022

(54) METHOD FOR DETERMINING ANNULUS SIZE OF BICUSPID VALVE (71) Applicants: THE ASAN FOUNDATION, Seoul (KR); UNIVERSITY OF ULSAN FOUNDATION FOR INDUSTRY COOPERATION, Ulsan (KR)

(72) Inventors: Dong Hyun Yang, Seoul (KR); June Goo Lee, Seoul (KR); Hyun Jung Koo, Seoul (KR); Jung-Min Ahn, Seoul (KR)

(73) Assignees: THE ASAN FOUNDATION, Seoul (KR); UNIVERSITY OF ULSAN FOUNDATION FOR INDUSTRY COOPERATION, Ulsan (KR)

(*) Notice: Subject to any disclaimer, the term of this patent is extended or adjusted under 35 U.S.C. 154(b) by 40 days.

(21) Appl. No.: 17/052,321

(22) PCT Filed: Apr. 22, 2019

(86) PCT No.: PCT/KR2019/004838
§ 371 (c)(1),
(2) Date: Nov. 2, 2020

(87) PCT Pub. No.: WO2019/212179
PCT Pub. Date: Nov. 7, 2019

(65) Prior Publication Data
US 2021/0241481 A1   Aug. 5, 2021

(30) Foreign Application Priority Data

May 3, 2018  (KR) .................. 10-2018-0051382

(51) Int. Cl.
*G06K 9/00*     (2022.01)
*G06T 7/60*     (2017.01)
(Continued)

(52) U.S. Cl.
CPC .............. *G06T 7/60* (2013.01); *G06T 7/0012* (2013.01); *A61B 5/0044* (2013.01); *A61B 5/055* (2013.01);
(Continued)

(58) Field of Classification Search
CPC ....................................................... G06T 7/60
See application file for complete search history.

(56) References Cited

U.S. PATENT DOCUMENTS

2007/0014452 A1* 1/2007 Suresh ............... G06T 7/0012
382/128
2007/0288000 A1* 12/2007 Bonan .................... A61B 6/481
606/1
(Continued)

FOREIGN PATENT DOCUMENTS

JP    07-255703 A    10/1995
JP    2007-319689 A   12/2007
(Continued)

OTHER PUBLICATIONS

International Search Report dated Jul. 11, 2019 in corresponding International Application No. PCT/KR2019/004838; 5 pages.

*Primary Examiner* — Oneal R Mistry
(74) *Attorney, Agent, or Firm* — Maier & Maier, PLLC (57) ABSTRACT

A method for determining the size of a bicuspid annulus of bicuspid, including acquiring an image of the heart including the left ventricle and the aorta; generating a first plane, which includes a line that passes through two base points in the bicuspid of the image of the heart; and generating multiple second planes, which are obtained per each rotation, while rotating the first plane multiple times by a predetermined angle about the line that passes through the two base points; measuring the cross-sectional area of each of at least one of the left ventricle and the aorta, which are formed on the first plane and the multiple second planes;
(Continued)

selecting a plane for measuring the size of a bicuspid annulus among the first plane and the multiple second planes based on the measured cross-sectional area; and measuring the size of the bicuspid annulus based on the selected plane.

8 Claims, 8 Drawing Sheets

(51) Int. Cl.
*G06T 7/00* (2017.01)
*A61B 5/00* (2006.01)
*A61B 5/055* (2006.01)
*A61B 6/03* (2006.01)
*A61B 6/00* (2006.01)
*A61B 8/08* (2006.01)

(52) U.S. Cl.
CPC ............ *A61B 6/032* (2013.01); *A61B 6/503* (2013.01); *A61B 8/0883* (2013.01); *G06T 2207/10081* (2013.01); *G06T 2207/10088* (2013.01); *G06T 2207/10132* (2013.01); *G06T 2207/30048* (2013.01); *G06T 2207/30101* (2013.01)

(56) References Cited

U.S. PATENT DOCUMENTS

| | | | | |
|---|---|---|---|---|
| 2008/0097210 | A1* | 4/2008 | Salgo | G06T 7/251 600/445 |
| 2010/0142787 | A1* | 6/2010 | Zheng | G06T 7/11 382/131 |
| 2015/0020547 | A1* | 1/2015 | Akita | A61B 17/00 66/232 |
| 2015/0320399 | A1* | 11/2015 | Chono | G16H 50/30 382/131 |
| 2016/0038246 | A1* | 2/2016 | Wang | G06T 7/73 600/587 |

FOREIGN PATENT DOCUMENTS

| | | |
|---|---|---|
| JP | 2011-239889 A | 12/2011 |
| KR | 10-2007-0110837 A | 11/2007 |
| KR | 10-2014-0002998 A | 1/2014 |
| KR | 20170134548 A | 12/2017 |

\* cited by examiner

METHOD FOR DETERMINING ANNULUS SIZE OF BICUSPID VALVE

TECHNICAL FIELD

The present disclosure relates to a method for determining the size of a bicuspid annulus of a bicuspid using image data of the heart.

BACKGROUND

The heart has heart valves that prevent backflow of blood, allowing blood to flow in only one direction. Heart valves with diseases such as stenosis can be treated by a surgical method. A general surgical method involves controlling the blood flow by a heart-lung bypass machine in a state where the heart is stopped, during which surgery is performed by incising the heart under anesthesia. This procedure is invasive and may expose a patient to a side effect such as infection. Accordingly, there is a growing interest in surgical methods for treating heart valves by minimizing invasion, for example, trans-catheter aortic valve implantation (TAVI). The surgical method for minimizing invasion needs to involve a procedure of generating an incision part in the skin of a patient less than a predetermined size, inserting a prosthetic valve into the body through the incision part, and fixing it in the heart valve region. The prosthetic valve used in such surgery can effectively perform the role as a heart valve as its size becomes similar to that of a patient's heart valve. Therefore, it is necessary to measure the size of the heart valve before surgery in order to determine the size of the prosthetic valve to be inserted.

Meanwhile, the heart valve includes a bicuspid located between the left ventricle and the left atrium, and a tricuspid located between the right atrium and the right ventricle. The bicuspid and tricuspid are not only located in different positions, but also have different shapes with each other. In the case of a bicuspid, it generally consists of two pocket-shaped leaflets and has two base points, whereas in the case of tricuspid, it consists of three pocket-shaped leaflets and has three base points. In this respect, when the size of a patient's heart valve is measured before surgery, in the case of a tricuspid, since only one plane that passes through the three base points can be determined based on three base points, the size of tricuspid can be measured. However, in the case of a bicuspid, since a plane cannot be determined among planes that pass through the two base points, and thus, there is a difficulty in measuring the size of a bicuspid in the same manner as the size of a tricuspid is measured.

PRIOR ART DOCUMENT

Patent Document (Patent Document 1) Korean Patent Application Publication No. 10-2017-7031325, method and apparatus for treating valvular disease (published on Dec. 6, 2017)

SUMMARY

The problem to be solved by the present disclosure is to determine the size of a bicuspid by measuring the size of a bicuspid annulus of a bicuspid using an image of the heart.

However, the problem to be solved by the present disclosure is not limited to those mentioned above, and the problem not mentioned above may include objects that can be clearly understood by those skilled in the art from the following description.

In accordance with one aspect of the present disclosure, there is provided a method for determining the size of a bicuspid annlus of bicuspid, comprising: acquiring an image of the heart comprising the left ventricle and the aorta; generating a first plane, which comprises a line that passes through two base points in the bicuspid of the image of the heart; and generating multiple second planes, which are obtained per each rotation, while rotating the first plane multiple times by a predetermined angle about the line that passes through the two base points; measuring the cross-sectional area of each of at least one of the left ventricle and the aorta, which are formed on the first plane and the multiple second planes; selecting a plane for measuring the size of a bicuspid annulus among the first plane and the multiple second planes based on the measured cross-sectional area; and measuring the size of the bicuspid annulus based on the selected plane.

Also, the angle rotated multiple times by the predetermined angle may be 360°.

Also, the bicuspid may be a bicuspid without a raphe.

Also, the plane for measuring the size of the bicuspid annulus may be a plane having the smallest cross-sectional area among the measured cross-sectional areas.

Also, the measuring the size of the bicuspid annulus may comprise: measuring the smallest cross-sectional area; and determining the size of the bicuspid annulus based on the size of the smallest cross-sectional area. Also, the image of the heart may be at least one among a computed tomography (CT) image, a magnetic resonance imaging (MRI) image, and an echocardiography image.

In accordance with another aspect of the present disclosure, there is provided a method for determining the size of a bicuspid annlus of bicuspid, comprising: acquiring an image of the heart comprising the left ventricle and the aorta; generating a first plane that passes through the sinus of Valsalva of the bicuspid, with respect to the bicuspid that passes through three base points comprising a raphe of the image of the heart; generating multiple second planes by moving the first plane in parallel by a predetermined interval in the direction of the left ventricle outflow; and in a case when the three base points disappear from the multiple second planes, measuring the size of the bicuspid annulus based on the plane generated immediately before the last parallel movement among the multiple second planes.

In accordance with another aspect of the present disclosure, there is provided a system for determining the size of a bicuspid annlus of bicuspid, comprising: an image acquisition unit, which acquires an image of the heart comprising the left ventricle and the aorta; a plane generation unit, which generates a first plane comprising a line that passes through two base points in the bicuspid of the image of the heart; and generates multiple second planes, by rotating the first plane multiple times by a predetermined angle about the line that passes through the two base points; a cross-sectional area measurement unit, which measures the cross-sectional area of each of at least one of the left ventricle and the aorta, which are formed on the first plane and the multiple second planes; a plane selection unit, which selects a plane for measuring the size of the bicuspid annulus among the first plane and the multiple second planes based on the measured cross-sectional area; and a bicuspid annulus size measurement unit, which measures the size of the bicuspid annulus based on the selected plane.

In accordance with another aspect of the present disclosure, there is provided a computer program stored in a computer-readable recording medium for causing a processor to perform at least one method among the methods described above.

In accordance with the other aspect of the present disclosure, there is provided a computer-readable recording medium on which a computer program comprising instructions for causing a processor to perform at least one method among the methods described above.

Advantageous Effects of the Invention

According to an embodiment of the present disclosure, it is possible to determine the size of a bicuspid having two base points using an image of the heart. More specifically, in an embodiment of the present disclosure, it is possible to determine the size of a bicuspid by obtaining a plane that passes through two base points of a bicuspid using the image data of the heart, and measuring the size of a bicuspid annulus of the bicuspid appearing on the plane using the same.

The effects that can be obtained from the present disclosure are not limited to the effects mentioned above, and other effects not mentioned can be clearly understood by those of ordinary skill in the technical field to which this disclosure belongs from the following description.

DETAILED DESCRIPTION

The advantages and features of exemplary embodiments of the present disclosure and methods of accomplishing them will be clearly understood from the following description of the embodiments taken in conjunction with the accompanying drawings. However, the present disclosure is not limited to those embodiments and is implemented in various forms. It is noted that the embodiments are provided to make a full disclosure and also to allow those skilled in the art to know the full scope of the present disclosure.

In the following description, well-known functions and/or configurations will not be described in detail if they would unnecessarily obscure the features of the disclosure. Further, the terms to be described below are defined in consideration of their functions in the embodiments of the disclosure and vary depending on a user's or operator's intention or practice. Accordingly, the definition is made on a basis of the content throughout the present disclosure.

Figure 1:
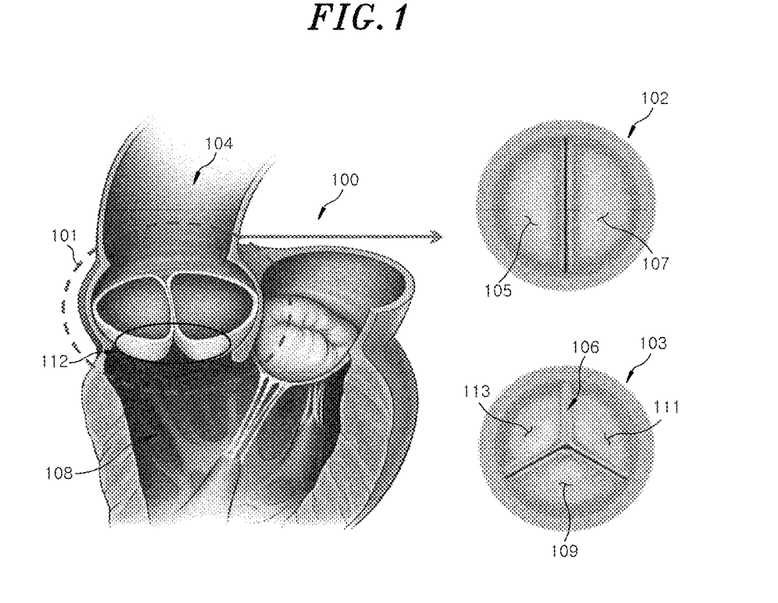
FIG. 1 shows an example of a typical bicuspid.

FIG. 1 shows an example of a typical bicuspid. The bicuspid (or bicuspid valve) 101, which is a part of a patient's heart 100, may be a term that refers to a constitution which prevents the backflow of blood between the aorta 104 and the left ventricle 108. The bicuspid 101 may include two leaflets and a bicuspid annulus 112 that supports the valve around the valve. When viewed from the direction in which the aorta 104 is located, the two leaflets may have a concave shape in the center. With this shape, each leaflet may include a base point, which is the most concave point.

Meanwhile, the bicuspid 101 may have different shapes depending on the person. Specifically, the bicuspid 101 may have a shape of a bicuspid 102 that does not include a raphe (or seam) 106 or a bicuspid 103 that includes a raphe 106. In the case of the bicuspid 102 not including the raphe 106, each of the leaflets has one base point, and accordingly, the bicuspid 102 may have two base points 105 and 107. In the case of the bicuspid 103 including the raphe 106, because a typical leaflet has one base point 109, and the leaflet including the raphe 106 is divided into two by the raphe 106, and accordingly, the bicuspid 103 including the raphe 106 may have two base points 111 and 113 for each of the divided spaces. That is, the bicuspid 103 including the raphe 106 may have three base points 109, 111, and 113. In the description of the present disclosure to be described later, a method of determining the size of the bicuspid annulus 112 of the bicuspids 101, 102, and 103 according to the presence/absence of the raphe 106 (i.e., the number of base points) will be described separately.

Figure 2:
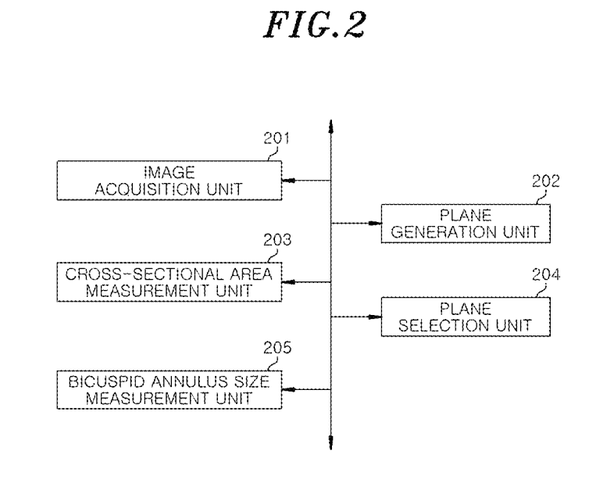
FIG. 2 shows a functional block diagram of a system for determining the size of a bicuspid annulus of a bicuspid according to an embodiment of the present disclosure.

FIG. 2 shows a functional block diagram of a system (or device) for determining the size of a bicuspid annulus of a bicuspid according to an embodiment of the present disclosure. As used herein below, the terms such as " . . . unit", " . . . device", etc. refers to a unit that processes at least one function or operation, and this may be implemented by hardware or software, or a combination of hardware and software.

Referring to FIG. 2, the system for determining the size of the bicuspid annulus 112 of the bicuspid may include an image acquisition unit 201, a plane generation unit 202, a cross-sectional area measurement unit 203, a plane selection unit 204, and a bicuspid annulus size measurement unit 205.

In an embodiment of the present disclosure, the image acquisition unit 201 can acquire an image of the heart including the left ventricle and the aorta. The image of the heart may include image data of a patient's heart. For example, the image of the heart may be at least one among a computed tomography (hereinafter, CT) image, a magnetic resonance imaging (hereinafter, MRI) image, and an echocardiography (or 3-dimensional echocardiography) image, and the heart image may include the bicuspid, the aorta, and the left ventricle. For example, the heart image may be a CT image of the heart which includes the aorta on the upper side and the left ventricle on the lower side being centered on the bicuspid. According to an embodiment, the heart image may be a heart image captured by the image acquisition unit 201 or a heart image received by an external device. The method of acquiring a heart image by the image acquisition unit 201 is not limited to the embodiments described above, but the heart image may be acquired in various ways.

The plane generation unit 202 can generate a plane for measuring the size of the bicuspid annulus 112 by using a heart image acquired by the image acquisition unit 201. The heart image may be an image of a patient's heart having the bicuspid 102 that includes two base points. In this case, the plane generation unit 202 can generate a first plane including a line that passes through two base points in the bicuspid 102 of the heart image. The plane generation unit 202 can generate a second plane each time when the first plane is rotated by a predetermined angle around a line that passes through the two base points, and may rotate multiple times (N times). That is, the plane generation unit 202 can generate multiple second planes corresponding to each rotation angle. The angle rotated N times by a predetermined angle may be 360°. For example, the multiple second planes may be a plane group including 360 planes generated by rotating 360 times by an angle of 1°. However, the predetermined angle is not limited to the embodiments described in this specification. The explanations related to the generation of the first plane and the rotation of the first plane will be described later through the explanation of FIG. 4.

Meanwhile, each of the first plane and the multiple second planes may include a portion related to the bicuspid 102. For example, each of the first plane and the multiple second planes may include a portion corresponding to at least one cross-section of the aorta and the left ventricle. For another example, the first plane and the multiple second planes may include a cross-section of the aorta and a cross section of the left ventricle, and another portion of the first plane and the multiple second planes may include one of the cross-section of the aorta and the cross-section of the left ventricle. According to an embodiment, a portion corresponding to at least one cross-section of the aorta and the left ventricle may include the bicuspid and the left ventricle outflow. Specific embodiments of the first plane and the multiple second planes will be described later through the explanations on FIGS. 5 and 6.

The cross-sectional area measurement unit 203 can measure each of the cross-sectional areas of the left ventricle and the aorta which are formed on the multiple second planes generated, by rotating the first plane multiple times (1 to N times) by a predetermined angle about the line that passes through two base points. For example, when at least one includes the cross-sectional area of the left ventricle and the cross-sectional area of the aorta on the plane of the first plane and the multiple second planes, the cross-sectional area measurement unit 203 can measure each cross-sectional area, whereas when either one is included, the cross-sectional area measurement unit 203 can measure the corresponding cross-sectional area. That is, the cross-sectional area measurement unit 203 can measure the cross-sectional area of the portion, where the cross-section corresponding to the left ventricle or the aorta is formed on the plane of the left ventricle or the aorta, which is included in the first plane and the multiple second planes.

The plane selection unit 204 can select a plane for measuring the size of the bicuspid annulus 112 among the first plane and the multiple second planes based on the measured cross-sectional area. The plane for measuring the size of the bicuspid annulus 112 may be a plane which has the smallest cross-sectional areas of the left ventricle and the aorta measured on each plane. In this case, the plane selection unit 204 can compare the sizes of each of the measured cross-sectional areas, and select a plane having the smallest cross-sectional area as a plane for measuring the size of the bicuspid annulus 112.

The bicuspid annulus size measurement unit 205 can measure the size of the bicuspid annulus 112 based on the selected plane. The bicuspid annulus size measurement unit 205 can measure the size of the bicuspid annulus 112 by measuring the diameters of the left ventricle and the aorta included in the selected plane. In some cases, the size of the bicuspid annulus 112 may be determined by the length of the perimeter surrounding the cross-sectional areas of the left ventricle and the aorta.

In another embodiment of the present disclosure, the plane generation unit 202 can generate a first plane that passes through the sinus of Valsalva of the bicuspid 103 to measure the size of the bicuspid annulus 112 of the bicuspid 103 including a raphe using a heart image. The plane generation unit 202 can generate multiple second planes by moving the first plane in parallel by a predetermined interval in the direction of the left ventricle outflow. The plane selection unit 204 can select a plane for measuring the size of the bicuspid annulus 112 among the first plane and the multiple second planes. The plane for measuring the size of the bicuspid annulus 112 may be a plane which, while including three base points of the first plane and the multiple second planes, is generated just before the final parallel movement in a case where the three base points disappear in the plane generated by parallel movement thereafter. The bicuspid annulus size measurement unit 205 can measure the size of the bicuspid annulus 112 based on at least one of the left ventricle and the aorta included in the selected plane. The explanation related to the measurement of the size of the bicuspid annulus 112 of the bicuspid 103 will be described later with reference to FIGS. 7 and 8.

As such, the system for determining the size of the bicuspid annulus 112 of the bicuspid according to an embodiment of the present disclosure can determine the size of a prosthetic valve suitable for the patient before surgery, by determining the size of the bicuspid annulus 112 based on the heart image. In some cases, the system can also be used for the purpose of obtaining information about the bicuspid annulus 112, which will be used to determine as to the possibility of prosthetic valve replacement or whether necessity of bicuspid annulus expansion. In addition, the present disclosure can be utilized in various fields using the size of the bicuspid annulus 112 as predetermined information.

The image acquisition unit 201, the plane generation unit 202, the cross-sectional area measurement unit 203, the plane selection unit 204, and the bicuspid annulus size measurement unit 205 described above may be directly connected or may be indirectly connected with a specific component interposed therebetween. Although not shown, the image acquisition unit 201, the plane generation unit 202, the cross-sectional area measurement unit 203, the plane selection unit 204, and the bicuspid annulus size measurement unit 205 may be implemented by an operation of at least one processor. In some cases, at least some of the image acquisition unit 201, the plane generation unit 202, the cross-sectional area measurement unit 203, the plane selection unit 204, and the bicuspid annulus size measurement unit 205 may be implemented by the same processor. The hardware or software associated with the system for determining the size of the bicuspid annulus 112 of bicuspid may be configured in various ways capable of performing the operation described below, and is not limited to the embodiments described above.

Additionally, although not shown, the system for determining the size of the bicuspid annulus 112 shown in FIG.

2 may include various configurations, for example memory, to determine the size of the bicuspid annulus 112. That is, the system for determining the size of the bicuspid annulus 112, although not shown in FIG. 2, may include various configurations for determining the size of the bicuspid annulus 112, and is not limited to the embodiments described above.

Figure 3:
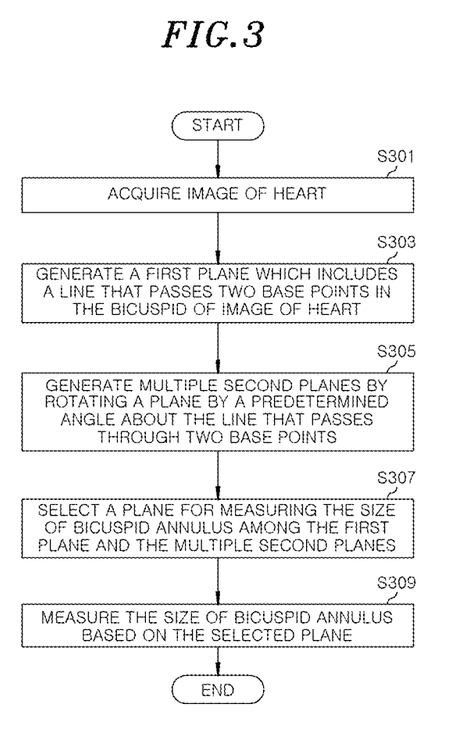
FIG. 3 shows an example of a flow of operations for determining the size of a bicuspid annulus of a bicuspid according to an embodiment of the present disclosure.

FIG. 3 shows an example of a flow of operations for determining the size of a bicuspid annulus of a bicuspid according to an embodiment of the present disclosure. The flow of the operation of FIG. 3 is a flow of the operation for determining the size of the bicuspid annulus 112 of a bicuspid that does not include a raphe, that is, has two base points.

Referring to FIG. 3, the image acquisition unit 201 can acquire a heart image including the left ventricle and the aorta (S301). The image of the heart including the left ventricle and the aorta may further include the bicuspid and the left ventricle outflow. The heart image may be image data of a patient's heart, for example, a CT image, an MRI, image, or an echocardiographic image. The heart image may be a heart image captured by the image acquisition unit 201 or a heart image received by an external device.

The plane generation unit 202 can generate a first plane which includes a line passing through the two base points in the bicuspid 102 of the heart image (S303). The bicuspid 102, which does not include a raphe, can have two base points. Although not shown, the plane generation unit 202 can identify two base points in the heart image based on the information about the previously stored feature points. The operation of identifying two base points based on the information about feature points can employ various existing feature points-based information extraction methods. According to an embodiment, the plane generation unit 202 can identify two base points based on receiving an input for setting two base points after acquiring the heart image. However, the plane generation unit 202 is not limited to the embodiments described above, but can identify two base points in various ways.

The plane generation unit 202 can identify two base points and generate a line connecting the two base points in the heart image. The plane generation unit 202 can generate a predetermined plane including the generated line, that is, a first plane. The plane generation unit 202 can rotate the first plane multiple times (N times) by a predetermined angle about a line that passes through the two base points, and thereby generate multiple second planes obtained for each rotation (S303). Since the plane which includes one line in common may be multiple, the plane generation unit 202 can generate a second plane each time a line passing through the two base points is rotated by a predetermined angle, and can rotate it multiple times (N times). That is, the plane generation unit 202 can generate multiple second planes corresponding to each rotation angle. The angle rotated N times by a predetermined angle may be an angle of 360°. For example, the multiple second planes may be a plane group including 360 planes generated by rotating 360 times by an angle of 1°.

The cross-sectional area measurement unit 203 can measure the cross-sectional area of at least one of the left ventricle and the aorta formed on the first plane and the multiple second planes, respectively. At least a portion of the aorta and the left ventricle may be included on the first plane and the multiple second planes, and the cross-sectional area measurement unit 203 can measure the cross-sectional area of a portion corresponding to at least one cross-section of the aorta and the left ventricle. For example, in the case where the cross-sectional area of a portion corresponding to the left ventricle and the cross-sectional area of a portion corresponding to the aorta are included in at least one on the first plane and the multiple second planes, the cross-sectional area measurement unit 203 can measure both of each cross-sectional area, and in the case where either one is included, the cross-sectional area measurement unit 203 can measure the cross-sectional area included. That is, the cross-sectional area measurement unit 203 can measure the cross-sectional area of the portion, where the cross-section corresponding to the left ventricle or the aorta is formed on a plane among the left ventricle or the aorta included in the first plane and the multiple second planes.

The plane selection unit 204 can select a plane for measuring the size of the bicuspid annulus 112 among the first plane and the multiple second planes based on the cross-sectional area measured (S307). The plane selection unit 204 can determine the plane to measure the size of the bicuspid annulus 112 by comparing the cross-sectional areas measured for each of the first plane and the multiple second planes. The plane for measuring the size of the bicuspid annulus 112 may be a plane which has the smallest cross-sectional area of the left ventricle and the aorta measured on each plane.

The bicuspid annulus size measurement unit 205 can measure the size of the bicuspid annulus 112 based on the selected plane (S309). The bicuspid annulus size measurement unit 205 can measure the size of the bicuspid annulus 112 based on the size of the cross-sectional area of the left ventricle and the aorta included in the selected plane. The size of the bicuspid annulus 112 may be the size of the diameters of the cross-sectional area of the left ventricle and the aorta included in the selected plane. In some cases, the size of the bicuspid annulus 112 may be determined by the length of the perimeters surrounding the cross-sectional area of the left ventricle and the aorta.

Figure 4:
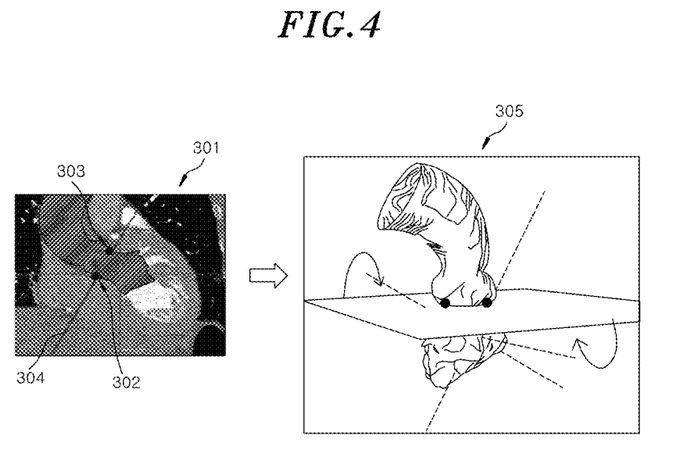
FIG. 4 shows an example of an operation for determining multiple planes that pass through the base points of a bicuspid according to an embodiment of the present disclosure.

FIG. 4 shows an example of an operation for determining multiple planes that pass through the base points of a bicuspid according to an embodiment of the present disclosure. The heart image 301 illustrated in FIG. 4 may be a heart image of a patient who has the bicuspid 102 including two base points 302 and 303.

The image acquisition unit 201 can acquire a heart image 301 including the aorta and the left ventricle. The plane generation unit 202 can identify the acquired heart image 301 and thereby generate a first plane 304 which includes a line passing through the two base points 302 and 303.

The plane generation unit 202 can generate multiple second planes by rotating the first plane 304 as shown in the image 305. Although a rotation in a clockwise direction is shown in the image 305, a rotation in a counterclockwise direction is also possible according to an embodiment. However, although not shown, the plane generation unit 202 can generate a plane (multiple second planes) which includes at least one of the left ventricle and the aorta at each predetermined angle by rotating the first plane based on the predetermined angle.

Figure 5:
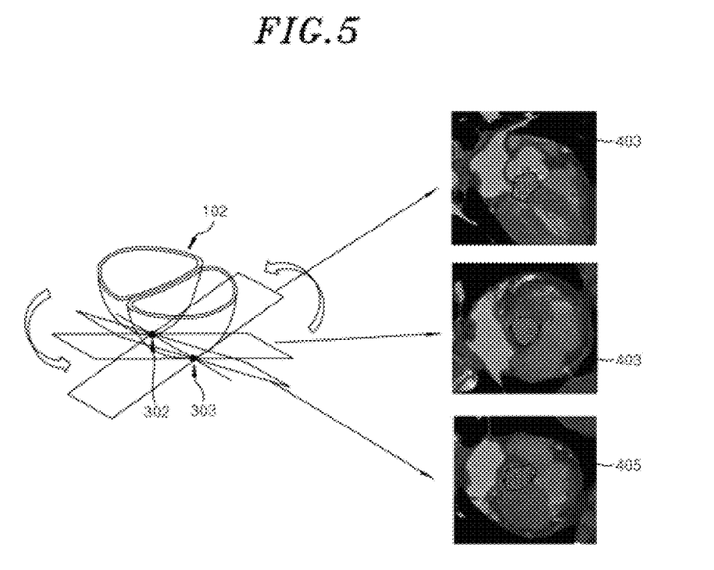
FIG. 5 shows an example of multiple planes that pass through the base points of a bicuspid according to an embodiment of the present disclosure.

FIG. 5 shows an example of multiple planes that pass through the base points of a bicuspid according to an embodiment of the present disclosure. FIG. 5 shows an example of a first plane and multiple second planes which were generated by rotating by different angles, while including two base points of the bicuspid 102.

Referring to FIG. 5, the plane generation unit 202 can generate a first plane 405 which includes a line that passes through two base points 302 and 303 of the bicuspid 102. The plane generation unit 202 can generate a plane each time when the first plane 405 is rotated by a predetermined angle based on the line that passes through the two base points 302 and 303. The group of planes generated each time when the first plane 405 is rotated multiple times (N times) by a predetermined angle may be referred to as multiple second planes. The predetermined angle may be, for example, 30°, and in this case, a second plane 403, which is a plane rotated by 30° of the first plane, and a second plane 403, which is a plane rotated by 60° of the first plane, can be generated. As indicated by hatching in FIG. 5, each image may include a portion of at least one of the left ventricle and the aorta.

The cross-sectional area measurement unit 203 can measure a cross-sectional area of at least one of the left ventricle and the aorta which are included in each plane. Based on the measurement of the cross-sectional area, the plane selection unit 204 can select a plane that is easy to measure the size of the bicuspid annulus 112. A more detailed description related to this may be referred to FIG. 6.

Figure 6:
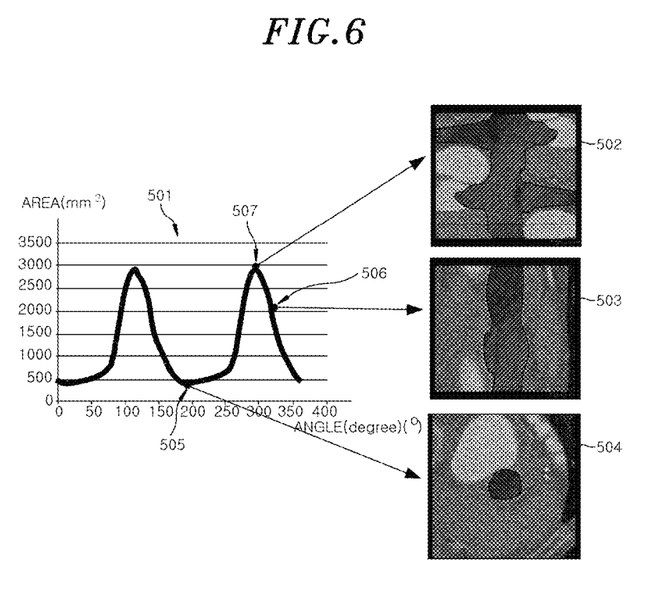
FIG. 6 shows an example of a graph for determining a plane to measure the size of a bicuspid annulus among the multiple planes that pass through the base points according to an embodiment of the present disclosure.

FIG. 6 shows an example of a graph for determining a plane to measure the size of a bicuspid annulus among the multiple planes that pass through the base points according to an embodiment of the present disclosure.

The graph 501 of FIG. 6 is a graph showing a cross-sectional area of at least one of the left ventricle and the aorta, which are included in the multiple second planes according to the rotation angle of the first plane for generating multiple second planes. Referring to the graph 501, the cross-sectional area of at least one of the left ventricle and the aorta represents a constant period including the minimum point 505 and the maximum point 507.

At each point, the minimum point 505 may appear as a plane 504, the maximum point 507 may appear as a plane 502, and any intermediate point 506 may appear as a plane 503. The plane selection unit 204 can determine a plane for determining the size of the bicuspid annulus 112 based on the information indicated by the graph 501. For example, the plane selection unit 204 may determine the plane 504 corresponding to the minimum point 505 as a plane for determining the size of the bicuspid annulus 112. In this case, the size of the bicuspid annulus 112 may be determined based on the cross-sectional area included in the plane 504. For example, the diameter of the cross-sectional area included in the plane 504 may be determined as the size of the bicuspid annulus 112.

Figure 7:
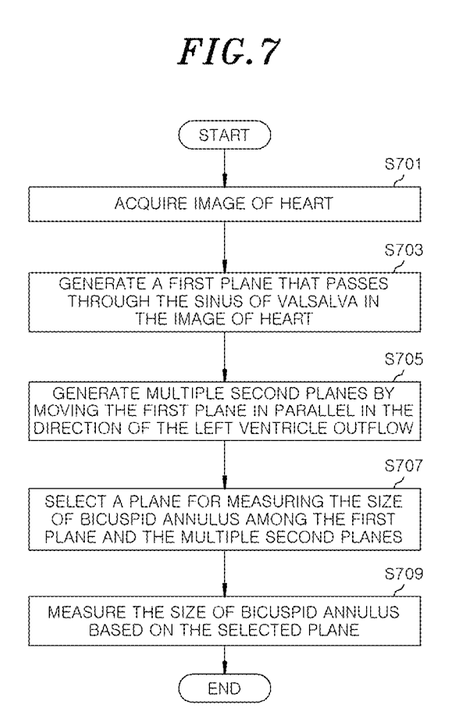
FIG. 7 shows an example of a flow of operations for determining the size of a bicuspid annulus of a bicuspid according to another embodiment of the present disclosure.

FIG. 7 shows an example of a flow of operations for determining the size of a bicuspid annulus of a bicuspid according to another embodiment of the present disclosure. The flow of operations of FIG. 7 is a flow of operations for determining the size of the bicuspid annulus 112 of the bicuspid 103, which includes the raphe, that is, which has three base points. Hereinafter, in the explanation of FIG. 7, the description overlapping with the explanation relating to a method of measuring the size of the bicuspid annulus of the bicuspid 102 having two base points may be omitted.

The image acquisition unit 201 can acquire an image of the heart (S701). The heart image may be an image of the bicuspid 103 including a raphe. In the case of the bicuspid 103 including a raphe, there may be 3 concave portions in the bicuspid 103, and a base point for each portion can be set.

The plane generation unit 202 can generate a first plane that passes through the Valsalva cavity in the heart image (S703). The first plane may be a plane having an inclination capable of passing through all of the three base points.

The plane generation unit 202 can move the first plane in the direction of the left ventricle outflow and thereby generate multiple second planes (S705). The direction of the left ventricle outflow may be a direction from the aorta to the left ventricle. The plane generation unit 202 can generate a second plane every time when the first plane moves in parallel by a predetermined interval in the direction of the left ventricle outflow, and can move in parallel multiple times (N times). In this case, the multiple second planes may be a plane group which includes N planes generated by moving in parallel N times by 1 mm.

The plane selection unit 204 can select a plane for measuring the size of the bicuspid annulus 112 among the first plane and the multiple second planes (S709). The plane for measuring the size of the bicuspid annulus 112, while including three base points of the multiple second planes, may be a plane at a point where three base points disappear in the plane generated thereafter. For example, while a plane which is generated at a distance moved in parallel downward from the first plane by 1 cm includes all of the three base points, a plane which is generated at a distance of more than 1 cm (e.g., a distance which is moved parallel to the lower side by 1.1 cm) may not include all of the three base points. In this case, the plane selection unit 204 may select a plane, which is generated from a distance moved in parallel downward by 1 cm from the first plane, as a plane for measuring the size of the bicuspid annulus 112.

The bicuspid annulus size measurement unit 205 can measure the size of the bicuspid annulus 112 based on the selected plane (S709). The first plane and the multiple second planes may include a cross-section of the aorta and a cross-section of the left ventricle, and another portion of the first plane and the multiple second planes may include either one of the cross-section of the aorta and the cross section of the left ventricle. The bicuspid annulus size measurement unit 205 can determine the cross-sectional areas of the left ventricle and the aorta in a selected plane and measure their diameters in the selected plane, in order to measure the size of the bicuspid annulus 112. The bicuspid annulus size measurement unit 205 may determine the diameter of the measured cross-sectional area as the size of bicuspid annulus 112.

Figure 8:
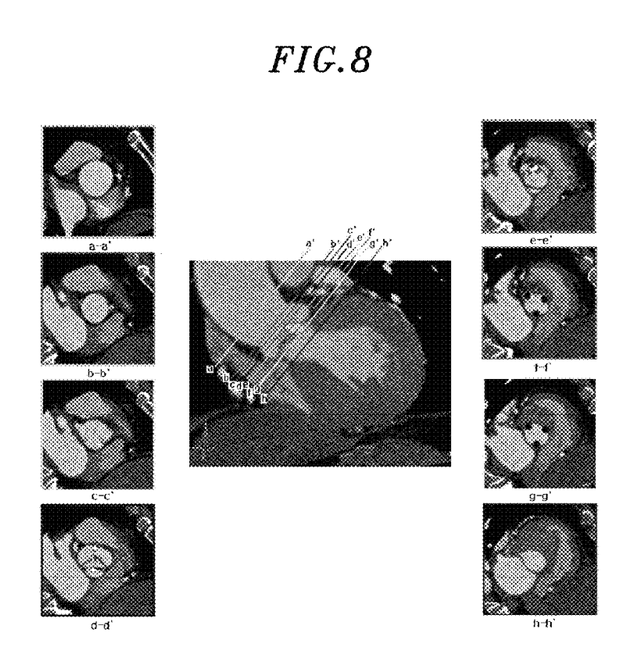
FIG. 8 shows an example of multiple planes for determining the size of a bicuspid annulus of a bicuspid according to another embodiment of the present disclosure.

FIG. 8 shows an example of multiple planes for determining the size of a bicuspid annulus 112 of a bicuspid according to another embodiment of the present disclosure, which is explained in FIG. 7.

Referring to FIG. 8, the plane generation unit 202 can generate multiple second planes while moving downward in parallel in the direction of the left ventricle outflow from the Valsalva cavity. The multiple second planes may include a-a', b-b', c-c', d-d', e-e', f-f', g-g', and h-h' shown in FIG. 8. In FIG. 8, three base points disappear from the plane with g-g' as the starting point in a plane, and in this case, the plane selection unit 204 may select g-g' as a plane for determining the size of the bicuspid annulus 112.

The combinations of the respective blocks of a block diagram and the combinations of the respective sequences of a flow diagram attached herein may be carried out by computer program instructions. Since the computer program instructions may be executed by the processor of a general purpose computer, a special purpose computer, or other programmable data processing apparatus, the instructions, executed by the processor of the computer or other programmable data processing apparatus, create means for performing functions described in the respective sequences of the flow diagram or the respective blocks of the block diagram. The computer program instructions, in order to implement functions in a specific manner, may be stored in a computer-readable storage medium or a computer-useable storage medium for other programmable data processing apparatus, and the instructions stored in the computer-readable storage medium or the computer-useable storage medium may produce manufacturing items that include means for instructions to perform the functions described in the respective sequences of the flow diagram or the respective blocks of the block diagram. The computer program instructions may be loaded in a computer or other programmable data processing apparatus, and therefore, the instructions, which are a series of sequences executed in a computer or other programmable data processing apparatus to create processes executed by a computer to operate a computer or other programmable data processing apparatus, may provide operations for executing functions described in the respective sequences of the flow diagram or the respective blocks of the block diagram.

Moreover, the respective block or the respective sequences may refer to two or more modules, segments, or codes including at least one executable instruction for executing a specific logic function(s). In some alternative embodiments, it is noted that the functions described in the sequences may be run out of order. For example, two consecutive sequences may be executed simultaneously or in reverse order according to the particular function.

The above description illustrates the technical idea of the present invention, and it will be understood by those skilled in the art to which this present invention belongs that various changes and modifications may be made without departing from the scope of the essential characteristics of the present invention. Therefore, the exemplary embodiments disclosed herein are not used to limit the technical idea of the present invention, but to explain the present invention, and the scope of the technical idea of the present invention is not limited by those embodiments. Therefore, the scope of protection of the present invention should be construed as defined in the following claims, and all technical ideas that fall within the technical idea of the present invention are intended to be embraced by the scope of the claims of the present invention.

What is claimed is:

1. A system for determining a size of a bicuspid annulus of bicuspid, the system comprising:
    an image acquisition unit which acquires an image of a heart comprising a left ventricle and an aorta;
    a plane generation unit which generates a first plane comprising a line that passes through two base points in the bicuspid of the image of the heart and generates multiple second planes by rotating the first plane multiple times by a predetermined angle about the line that passes through the two base points;
    a cross-sectional area measurement unit which measures the cross-sectional area of each of at least one of the left ventricle and the aorta, which are formed on the first plane and the multiple second planes;
    a plane selection unit which selects a plane for measuring the size of the bicuspid annulus among the first plane and the multiple second planes based on the measured cross-sectional area; and
    a bicuspid annulus size measurement unit which measures the size of the bicuspid annulus based on the selected plane.

2. A system for determining a size of a bicuspid annulus of bicuspid, the system comprising:
    an image acquisition unit which acquires an image of a heart comprising a left ventricle and an aorta;
    a plane generation unit which generates a first plane that passes through a sinus of Valsalva of the bicuspid, with respect to the bicuspid that passes through three base points comprising a raphe of the image of the heart, and generates multiple second planes by moving the first plane in parallel by a predetermined interval in the direction of the left ventricle outflow; and
    a bicuspid annulus size measurement unit which, in a case where the three base points disappear from the multiple second planes, measures the size of the bicuspid annulus based on the plane generated immediately before the last parallel movement among the multiple second planes.

3. The system of claim 1, wherein the angle rotated multiple times by the predetermined angle is 360°.

4. The system of claim 1, wherein the bicuspid is a bicuspid without a raphe.

5. The system of claim 1, wherein the plane for measuring the size of the bicuspid annulus is a plane having the smallest cross-sectional area among the measured cross-sectional areas.

6. The system of claim 5, wherein the bicuspid annulus size measurement unit measures the smallest cross-sectional area and determines the size of the bicuspid annulus based on the size of the smallest cross-sectional area.

7. The system of claim 1, wherein the image of the heart is at least one among a computed tomography (CT) image, a magnetic resonance imaging (MRI) image, and an echocardiography image.

8. A non-transitory computer-readable recording medium on which a program comprising instructions for causing a processor to perform a method for determining a size of a bicuspid annulus of bicuspid, the method comprising:
    acquiring an image of the heart comprising a left ventricle and an aorta;
    generating a first plane, which comprises a line that passes through two base points in the bicuspid of the image of the heart and generating multiple second planes, which are obtained per each rotation, while rotating the first plane multiple times by a predetermined angle about the line that passes through the two base points;
    measuring a cross-sectional area of each of at least one of the left ventricle and the aorta, which are formed on the first plane and the multiple second planes;
    selecting a plane for measuring the size of a bicuspid annulus among the first plane and the multiple second planes based on the measured cross-sectional area; and
    measuring the size of the bicuspid annulus based on the selected plane.

* * * * *